United States Patent [19]

Wilk

[11] Patent Number: 5,318,013
[45] Date of Patent: Jun. 7, 1994

[54] SURGICAL CLAMPING ASSEMBLY AND ASSOCIATED METHOD

[76] Inventor: Peter J. Wilk, 185 W. End Ave., New York, N.Y. 10023

[21] Appl. No.: 972,508

[22] Filed: Nov. 6, 1992

[51] Int. Cl.⁵ .............................................. A61B 17/00
[52] U.S. Cl. ...................................... 128/20; 606/205; 606/198; 128/898
[58] Field of Search .................... 128/20, 749, 898; 606/1, 51, 52, 110, 113, 127, 139–144, 151, 157, 198, 190, 205–208; 294/89.1, 102.1, 100, 115

[56] References Cited

U.S. PATENT DOCUMENTS

| | | | |
|---|---|---|---|
| 4,432,352 | 2/1984 | Wineland | 606/208 |
| 5,099,827 | 3/1992 | Melzer et al. | 606/142 |

FOREIGN PATENT DOCUMENTS

| | | | |
|---|---|---|---|
| 0035357 | 3/1930 | France | 606/208 |
| 0015314 | 8/1903 | United Kingdom | 606/198 |

*Primary Examiner*—Stephen C. Pellegrino
*Assistant Examiner*—Glenn Dawson
*Attorney, Agent, or Firm*—R. Neil Sudol; Henry D. Coleman

[57] ABSTRACT

A surgical device including a frame member having a distal end and a proximal end and a pair of clamping mechanisms movably mounted to the frame member at the distal end thereof for exerting respective clamping forces on spaced organic tissues of a patient. Actuators mounted to the frame member at the proximal end thereof are operatively connected to the clamping mechanisms for controlling the operation thereof. Another actuator, also mounted to the frame member, is operatively connected to the clamping mechanisms for increasing a distance therebetween, thereby stretching organic tissues between the clamped tissues and facilitating access to the stretched tissues. The instrument assembly is particularly useful during laparoscopic surgery.

11 Claims, 2 Drawing Sheets

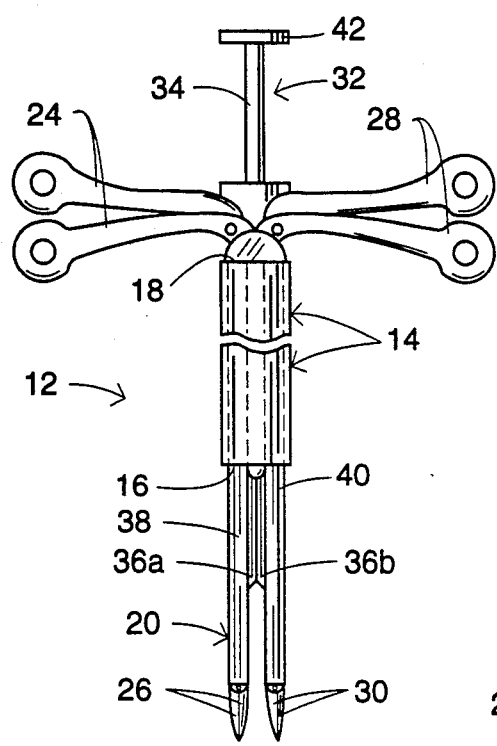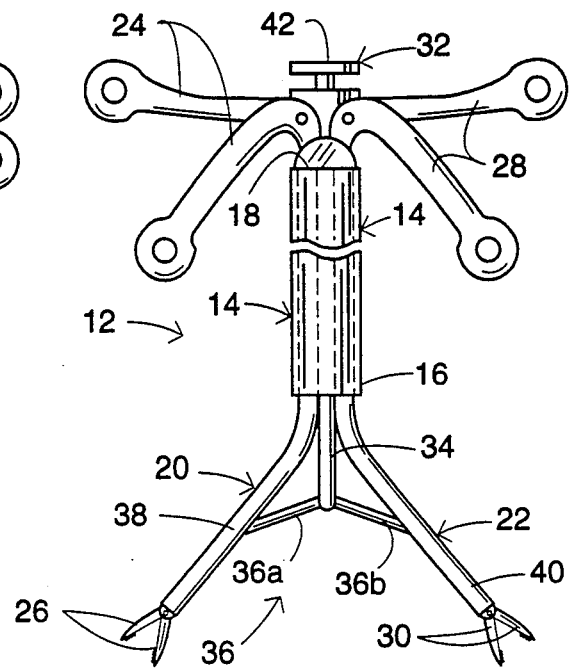
FIG. 1    FIG. 2
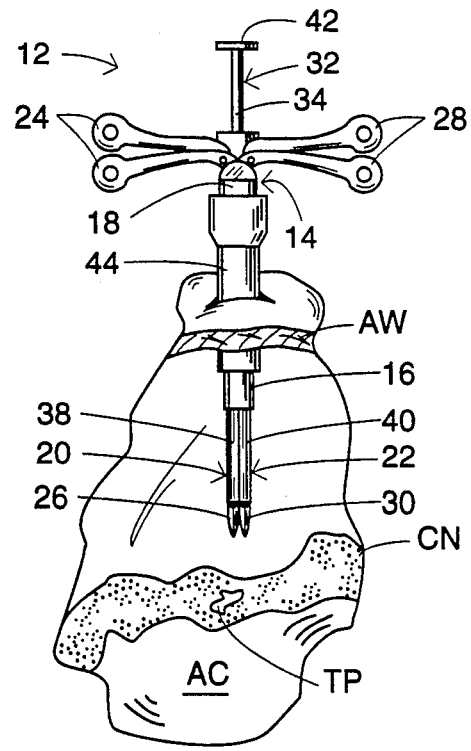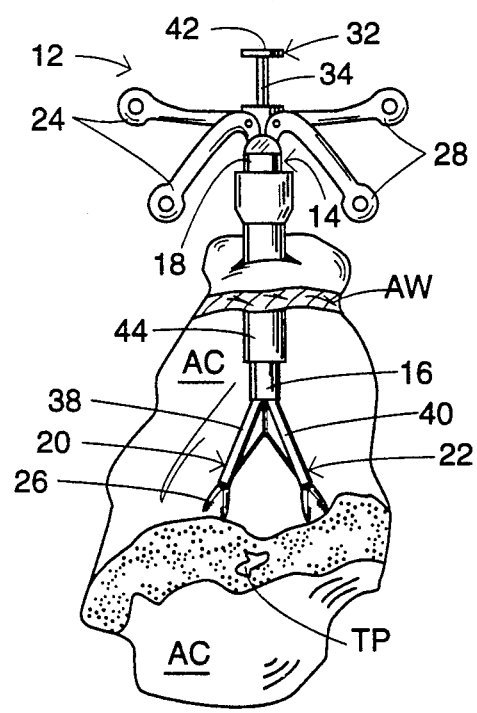
FIG. 3A    FIG. 3B

SURGICAL CLAMPING ASSEMBLY AND ASSOCIATED METHOD

BACKGROUND OF THE INVENTION

This invention relates to a surgical instrument assembly. More particularly, this invention relates to a clamping device for use in surgery. This invention also relates to an associated surgical method or procedure.

During surgical operations, one of the most important operations is the spreading of convoluted and folded organic tissues to enable visual inspection and physical access to a potential surgical site. Generally, such access is achieved by initially attaching a first clamp to tissues on one side of the desired site and a second clamp to tissues on the opposite side of the site. The clamps are then pulled apart, by surgical assistants, to spread the tissues between the two clamps.

Such a procedure, although useful and effective in open surgery, could be streamlined. In addition, the procedure is cumbersome if used in laparoscopic surgery.

Laparoscopy involves the piercing of a patient's abdominal wall and the insertion of a cannula through the perforation. Generally, the cannula is a trocar sleeve which surrounds a trocar during an abdomen piercing operation. Upon the formation of the abdominal perforation, the trocar is withdrawn while the sleeve remains traversing the abdominal wall. A laparoscopic instrument, such as a laparoscope or a forceps, is inserted through the cannula so that a distal end of the instrument projects into the abdominal cavity.

Generally, in a laparoscopic surgical procedure, three or four perforations are formed in the abdomen to enable deployment of a sufficient number of laparoscopic instruments to perform the particular surgery being undertaken. Each perforation is formed by a trocar which is surrounded by a sleeve, the sleeves or cannulas all remaining in the abdominal wall during the surgical procedure.

Prior to insertion of the first trocar and its sleeve, a hollow needle is inserted through the abdominal wall to enable pressurization of the abdominal cavity with carbon dioxide. This insufflation procedure distends the abdominal wall, thereby producing a safety space above the patient's abdominal organs.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

To enable access to a desired surgical site during a laparoscopic operation, the tissue spreading procedure described above requires the formation of at least four abdominal perforations and the insertion of four trocar sleeves. Two sleeves are required for the clamps, another sleeve for the laparoscope and a fourth sleeve for an instrument (e.g., scalpel, forceps, cautery probe, etc.) to perform a surgical operation at the sugical site which has been made visible by the tissue spreading procedure.

OBJECTS OF THE INVENTION

An object of the present invention is to provide a surgical instrument assembly for use in spreading organic tissues of a patient during an operation.

Another, more particular, object of the present invention is to provide such an instrument assembly which is particularly useful in laparoscopic surgery.

A further particular object of the present invention is to provide such a laparoscopic instrument assembly which requires only one trocar sleeve.

Yet another object of the present invention is to provide an associated surgical technique for spreading organic tissues to facilitate access thereto.

These and other objects of the present invention will be apparent from the drawings and detailed descriptions herein.

SUMMARY OF THE INVENTION

A surgical device comprises, in accordance with the present invention, a frame member having a distal end and a proximal end, a first clamping mechanism movably mounted to the frame member at the distal end thereof for exerting a clamping force on first organic tissues of a patient, and a second clamping mechanism also movably mounted to the frame member at the distal end thereof for exerting a clamping force on second organic tissues of the patient spaced from the first organic tissues. A first actuator is mounted to the frame member at the proximal end thereof and is operatively connected to the first clamping mechanism for controlling the operation thereof, while a second actuator is mounted to the frame member at the proximal end thereof and is operatively connected to the second clamping mechanism for controlling the operation of that second clamping mechanism. A third actuator, also mounted to the frame member, is operatively connected to the clamping mechanisms for increasing a distance therebetween, thereby stretching organic tissues between the clamped tissues and facilitating access to the stretched tissues.

Pursuant to another feature of the present invention, at least one of the clamping mechanisms includes a pair of jaws.

Pursuant to a further feature of the present invention, the frame member is elongate and sufficiently thin to fit down a laparoscopic trocar sleeve.

Pursuant to yet another feature of the present invention, the clamping mechanisms are secured to the frame means via respective flexible shafts, and the third actuator includes an articulated linkage pivotably connected to the shafts. The linkage is alternately shiftable in a distal direction and a proximal direction for alternatively spacing and approximating the clamping mechanisms.

Other specific mechanisms are possible for spreading the clamps. Spreading may be accomplished by a screw mechanism or a camming mechanism.

A surgical method comprises, in accordance with the present invention, the steps of (a) providing a surgical instrument having two clamping mechanisms connected to one another, (b) operating the clamping mechanisms to clamp organic tissues of a patient at spaced points with the clamping mechanisms, and (c) exerting a force via the surgical instrument to increase a distance between the clamping mechanisms and concomitantly the spaced points, thereby stretching organic tissues between the spaced points.

According to another feature of the present invention, where the clamping mechanisms are disposed at distal ends of respective flexible shafts, the shafts are pressed apart from one another.

According to an additional feature of the present invention, the method further comprises the step of inserting a distal end portion of the surgical instrument, including the clamping mechanisms, through a laparoscopic trocar sleeve disposed in an abdominal wall of the patient. In that case, the the clamping mechanisms are operated only upon an emergence of the clamping mechanisms from a distal end of the trocar sleeve.

A surgical instrument assembly and associated method in accordance with the present invention for use in spreading organic tissues of a patient during an operation are particularly useful in laparoscopic surgery. Only one trocar sleeve is required. However, the method and instrument assembly may be used in open surgery as well.

BRIEF DESCRIPTION OF THE DRAWING

FIG. 1 is a schematic side elevational view of a laparoscopic surgical clamping assembly in accordance with the present invention, showing a pair of grasping forceps disposed in a mutually parallel insertion configuration and with closed grasping jaws.

FIG. 2 is a schematic side elevational view of the laparoscopic surgical clamping assembly of FIG. 1, showing the grasping forceps disposed in a spread-apart use configuration and with opened grasping jaws.

FIGS. 3A-3C are partial schematic cross-sectional views of a patient's abdomen with the surgical clamping assembly of FIGS. 1 and 2 inserted therein, the clamping assembly being illustrated in successive steps of a clamping and spreading operation in accordance with the present invention.

DETAILED DESCRIPTION

Figure 3C:
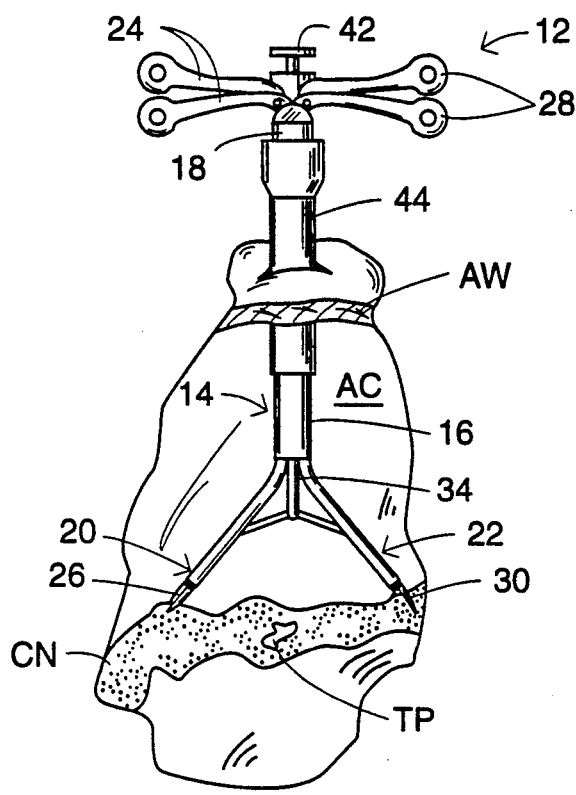

As illustrated in FIGS. 1 and 2, a surgical clamping device 12 for spreading or stretching clamped organic tissues comprises a frame member 14 having a distal end 16 and a proximal end 18. Two clamping mechanisms in the form of respective grasping forceps 20 and 22 are movably mounted to frame member 14 at distal end 16 thereof for exerting clamping forces on spaced organic tissues of a patient. A first actuator 24 is mounted to frame member 14 at proximal end 18 thereof and is operatively connected to grasping forceps 20 for controlling the opening and closing of jaws 26 of that forceps, while a second actuator 28 is mounted to frame member 14 at proximal end 18 and is operatively connected to grasping forceps 22 for alternately opening and closing jaws 30 of that grasping forceps. A third actuator 32 including a reciprocatable plunger element or push rod 34 is slidably mounted to frame member 14 and operatively connected to grasping forceps 20 and 22 for increasing the distance between jaws 26 and jaws 30, thereby stretching the clamped organic tissues and facilitating access to the stretched tissues.

As shown in FIG. 2, actuator 32 also includes an articulated linkage 36 comprising a pair of arms 36a and 36b pivotably connected to push rod 34 at the distal end thereof and pivotably connected to shafts 38 and 40 of respective grasping forceps 20 and 22. Shafts 38 and 40 are flexible in a region immediately distal of a distal end of frame member 14, thereby enabling a relative spreading of grasping forceps 20 and 22 from a straightened or mutually parallel insertion configuration of FIG. 1 to a spread use configuration if FIG. 2 upon a distally directed stroke of push rod 34. Push rod 34 is provided at a proximal end with a flange 42 for facilitating manual reciprocation of push rod 34.

FIGS. 3A-3C show a distal end portion of clamping device 12 inserted into an abdominal cavity AC of a patient through a laparoscopic trocar sleeve 44 itself traversing an abdominal wall AW of the patient. FIG. 3A illustrates an initial insertion configuration of clamping device 10 wherein push rod 34 is retracted in a proximal direction and grasping jaws 26 and 30 are closed. (This configuration is also used when the clamping device 12 is being withdrawn from abdominal cavity AC upon termination of the laparoscopic tissue spreading operation.)

Upon the insertion of the distal end portion of clamping device 12 into abdomianl cavity AC, push rod 34 may be shifted slightly in the distal direction, if desired, to partially separate jaws 26 and 30 of grasping forceps 20 and 22 (FIG. 3B). Actuators 24 and 28 are then operated to open jaws 26 and 30, whereupon device or instrument 12 is manipulated from outside the patient to grasp respective portions of organic tissue, for example, of the colon CN, on opposite sides of a traumatic injury or perforation TP. After a subsequent closure of jaws 26 and 30, push rod 34 is pushed further in the distal direction, as depicted in FIG. 3C, to spread the tissues of colon CN in the region about traumatic injury or perforation TP.

The stretching of the tissues of colon CN about perforation TP facilitates surgery by providing direct access to the injury. A suturing operation or other surgical treatment may be performed easily on traumatic perforation TP. Upon the closure of perforation TP, the steps illustrated in FIGS. 3A-3C are performed in reverse order.

Figure 4:
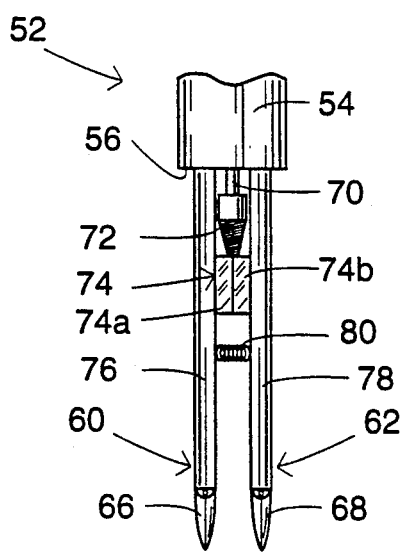
FIG. 4 is a partial schematic side elevational view of another laparoscopic surgical clamping assembly in accordance with the present invention, showing a pair of grasping forceps disposed in a mutually parallel insertion configuration and with closed grasping jaws.

As illustrated in FIG. 4, another surgical clamping device 52 for spreading or stretching clamped organic tissues comprises a frame member 54 having a distal end 56 and a proximal end (not shown). Two clamping or grasping forceps 60 and 62 are movably mounted to frame member 54 at distal end 56 thereof for exerting clamping forces on spaced organic tissues of a patient. Actuators (not shown) are mounted to frame member 54 at the proximal end thereof for controllably opening and closing jaws 66 of forceps 60 and jaws 68 of forceps 62. A third actuator includes a rotatable shaft 70 carrying a tapered screw 72 at a distal end. Upon a rotation of shaft 70, screw 72 is pulled into an internally threaded split bushing or nut 74. Nut 74 has a first half 74a attached to a partially flexible shaft 76 of forceps 60, while a second half 74b of nut 74 is fixed to a partially flexible shaft 78 of forceps 62. The entry of screw 72 into nut 74 causes the separation of halves 74a and 74b and consequently of forceps shafts 76 and 78 in opposition to an inherent spring force or a helical tension spring 80 extending between forceps shafts 76 and 78.

Figure 5:
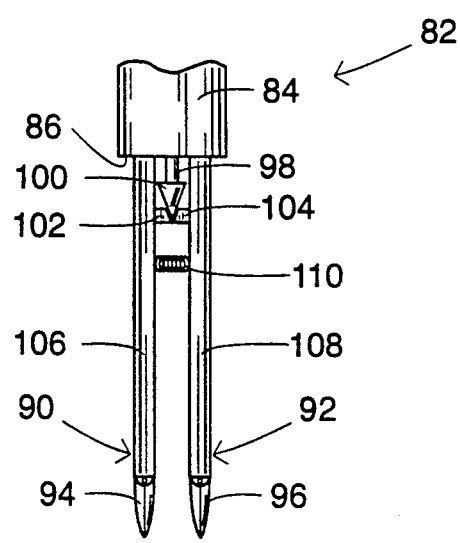
FIG. 5 is a partial schematic side elevational view of yet another laparoscopic surgical clamping assembly in accordance with the present invention, showing two grasping forceps parallel to one another insertion configuration and with closed grasping jaws.

As illustrated in FIG. 5, yet another surgical clamping device 82 for spreading or stretching clamped organic tissues comprises a frame member 84 having a distal end 86 and a proximal end (not illustrated). Two clamping or grasping forceps 90 and 92 are movably mounted to frame member 84 at distal end 86 thereof for exerting clamping forces on spaced organic tissues of a patient. Actuators (not shown) are mounted to frame member 84 at the proximal end thereof for controllably opening and closing jaws 94 of forceps 90 and closing jaws 96 of forceps 92. A third actuator includes a slidable shaft 98 carrying a wedge 100 at a distal end. Upon a sliding of shaft 98 in the distal direction, wedge 100 slidingly engages camming elements 102 and 104 which are attached to shafts 106 and 108 of forceps 90 and 92 and forces the shafts apart in opposition to an inherent spring force or a helical tension spring 110 extending between forceps shafts 106 and 108.

Although the invention has been described in terms of particular embodiments and applications, one of ordinary skill in the art, in light of this teaching, can generate additional embodiments and modifications without departing from the spirit of or exceeding the scope of the claimed invention. For example, the clamping action of grasping forceps 20 and 22 may be accomplished by other equivalent clamping devices. In some cases a hook or paw may perform a clamping or catching operation sufficient for spreading organic tissues as described herein.

Accordingly, it is to be understood that the drawings and descriptions herein are proffered by way of example to facilitate comprehension of the invention and should not be construed to limit the scope thereof.

What is claimed is:

1. A surgical device comprising:
    a frame member having a distal end and a proximal end;
    first clamping means secured to said frame member and disposed at said distal end thereof for exerting a clamping force on first organic tissues of a patient;
    second clamping means secured to said frame member and disposed at said distal end thereof for exerting a clamping force on second organic tissues of the patient spaced from the first organic tissues, at least one of said first clamping means and said second clamping means being movable relative to the other;
    first actuator means, mounted to said frame member at said proximal end thereof and operatively connected to said first clamping means, for controlling operation of said first clamping means;
    second actuator means, mounted to said frame member at said proximal end thereof and operatively connected to said second clamping means, for controlling operation of said second clamping means; and
    third actuator means, mounted to said frame member and operatively connected to said first clamping means and said second clamping means, for increasing a distance between said first clamping means and said second clamping means, thereby stretching third organic tissues between said first organic tissues and said second organic tissues and facilitating access to said third organic tissues.

2. The device defined in claim 1 wherein at least one of said first clamping means and said second clamping means includes a pair of jaws.

3. The device defined in claim 1 wherein said frame member is elongate and sufficiently thin to fit down a laparoscopic trocar sleeve.

4. The device defined in claim 1 wherein said first clamping means and said second clamping means are secured to said frame means via respective flexible shafts, said third actuator means including an articulated linkage pivotably connected to said shafts, said third actuator means further including means for alternately shifting said linkage in a distal direction and a proximal direction.

5. The device defined in claim 1 wherein said third actuator means includes an articulated linkage.

6. The device defined in claim 1 wherein said third actuator means includes a screw mechanism.

7. A surgical method comprising the steps of:
    providing a surgical instrument having two clamping mechanisms connected to one another;
    operating said clamping mechanisms to clamp organic tissues of a patient at spaced points with said clamping mechanisms; and
    exerting a force via said surgical instrument to increase a distance between said clamping mechanisms and concomitantly said spaced points, thereby stretching organic tissues between said spaced points.

8. The method defined in claim 7 wherein said clamping mechanisms are disposed at distal ends of respective flexible shafts, said step of exerting a force including the step of pressing said shafts apart from one another.

9. The method defined in claim 8 wherein said step of pressing includes the step of operating a screw mechanism.

10. The method defined in claim 8 wherein said step of pressing includes the step of moving an articulated linkage in a distal direction.

11. The method defined in claim 7, further comprising the step of inserting a distal end portion of said surgical instrument, including said clamping mechanisms, through a laparoscopic trocar sleeve disposed in an abdominal wall of the patient, said steps of operating and exerting being executed upon an emergence of said clamping mechanisms from a distal end of the trocar sleeve.

* * * * *